United States Patent [19]

Charpentier et al.

[11] Patent Number: 4,985,406

[45] Date of Patent: Jan. 15, 1991

[54] PEPTIDES DERIVED FROM CCK8, THEIR PREPARATION AND THE PHARMACEUTICAL COMPOSITIONS WHICH CONTAIN THEM

[75] Inventors: Bruno Charpentier, L'Hay Les Roses; Bernard P. Roques, Saint Maurice, both of France

[73] Assignee: Institut National de la Sante et de La Recherche Medicale (INSERM), France

[21] Appl. No.: 162,410

[22] Filed: Feb. 29, 1988

[30] Foreign Application Priority Data

Mar. 2, 1987 [FR] France ................. 87 02770

[51] Int. Cl.$^5$ .................... A61K 37/02; C07K 7/54
[52] U.S. Cl. ....................... 514/11; 530/317
[58] Field of Search ............... 530/317, 321, 323, 328, 530/329; 514/9, 11, 16

[56] References Cited

U.S. PATENT DOCUMENTS

| | | | |
|---|---|---|---|
| 3,705,140 | 12/1972 | Bernardi et al. | 424/177 |
| 3,981,303 | 9/1976 | Higuchi et al. | 424/428 |
| 4,490,364 | 12/1984 | Rivier et al. | 424/177 |
| 4,737,487 | 4/1988 | Watts et al. | 530/328 |
| 4,769,445 | 9/1988 | Comstock et al. | 530/328 |
| 4,808,701 | 2/1989 | Danho et al. | 530/317 |

OTHER PUBLICATIONS

Charpentier et al., J. Med. Chem. vol. 30, pp. 962–968 (1987).
Durieux et al., Papt:Struct. Funct; Proc. Am. Pept. Symp., 9th, pp. 575–578 Edited by:Deber et al. (1985).
Lehninger, Biochemistry, second Edition, The Molecular Basis of Cell Structure and Function, pp. 71–75 (1975) Worth Publishers, Inc.
Charpentier et al. J. Med. Chem., vol. 32, pp. 1184–1190 (1989).
Charpentier et al. Elsevier Science Publishers B.V. (Biomedical Division), Bali et al. (edi), pp. 33–36 (1987).
Cram et al., Organic Chemistry, 2nd Edi. McGraw-Hill Book Company, New York, pp. 607–613, (1964).

*Primary Examiner*—Johnnie R. Brown
*Assistant Examiner*—Christina Chan
*Attorney, Agent, or Firm*—Morgan & Finnegan

[57] ABSTRACT

Peptides of formula:

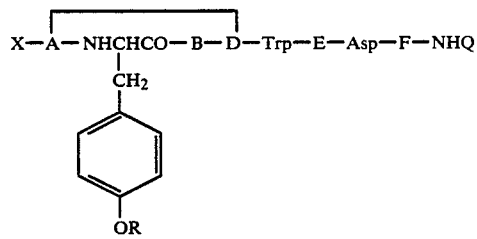

in which X=H or a radical which protects the amine gorup, R=H or SO$_3$H, A an D are:
either different, and one of them donotes a radical

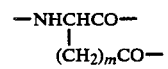

and the other a radical

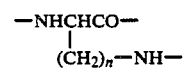

m and n being between 1 and 5, and A and D form a ring by amidation of their side chains,
or identical or different and denote:

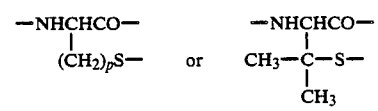

with p=1 or 2, and A and D form a ring by oxidative bridging between the sulphur atoms; B and E=Met, NLe, Leu, Ser, Thr, allo-Thr, or Cys or Hcy, in which the OH or SH groups are free or protected;
F=valency bond or Phe, Tyr(OCH$_3$) or Cha;
Q=H or alkyl (1 to 6 C), phenyl or phenylalkyl, these radicals being unsubstituted or substituted with fluorine atoms, and the amino acids are D, L or DL; are useful, in particular, as enuropsychotropic drugs.

2 Claims, No Drawings

PEPTIDES DERIVED FROM CCK8, THEIR PREPARATION AND THE PHARMACEUTICAL COMPOSITIONS WHICH CONTAIN THEM

The present invention relates to peptides exhibiting cholecystokininergic properties specific for receptors of the central nervous system, their preparation and the therapeutic compositions which contain them.

It is known that there are at least two types of cholecystokininergic receptors, of different molecular weights [SAKAMOTO et al., J. Biol. Chem. 258, 12707 (1983); SAKAMOTO et al., Biochem. Biophys. Res. Comm., 124, 497 (1984)], capable of binding the following sulphated octapeptide (known by the name of CCK8):

$$\text{Asp-Tyr(SO}_3\text{H)-Met-Gly-Trp-Met-Asp-Phe-NH}_2 \quad \text{(I)}$$

The receptors of the central nervous system and the receptors of the peripheral nervous system are thereby distinguished. At central nervous system level, CCK8 plays the part of a neurotransmitter [GOLTERMAN et al., J. Biol. Chem. 255, 6181 (1980)]. In addition, it is co-localized with dopamine in certain neurones of the mesolimbic pathway [HÖKFELT et al., Nature, 285, 476 (1980)]; it antagonizes the effects thereof in the mesolimbic system and facilitates dopaminergic neurotransmission in the striatum [FUXE et al., Eur. J. Pharmacol, 67, 329 (1980)]. As regards the peripheral receptors, these are involved in the contraction of smooth muscles at intestinal level [HUTCHINSON et al., Eur. J. Pharmacol., 69, 87 (1981); CHANG et al., Neuroscience Lett., 46, 71 (1984)] and in the release of pancreatic amylase [JENSEN et al., J. Biol. Chem., 257, 5554 (1982)].

CCK8, as well as other structurally related products, are known from German Patent Application No. 3,138,233 to have a neuropsychotropic action, but their value is mitigated by the fact that they are not devoid of peripheral activity.

The present invention provides CCK8 analogues which retain central nervous activity (which can be predicted by measuring their affinity for the cerebral receptors) but are if possible devoid of peripheral activity, or at least exhibit the latter to only a lesser degree (the peripheral activity being deduced from the measurement of the affinity of the products for the peripheral receptor sites).

Since it is known from experience that even very minor modification of one or more amino acids in a peptide produces substantial modifications in the activity, or even frequently complete loss of activity, of the peptide, the modifications to be made to CCK8 in order to achieve activity on central nervous receptors combined with little or no activity on peripheral receptors were far from obvious. The present invention provides, however, novel cyclic analogues of CCK8 in which this objective has been realised.

The peptides of the present invention have the formula:

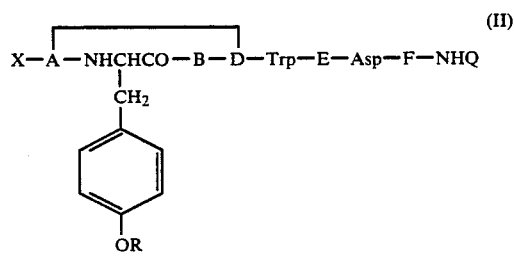

in which X denotes a hydrogen atom or a radical which protects the amine group which is either of the acyl type, such as formyl, acetyl, chloroacetyl, trifluoroacetyl, propionyl, butyryl, isobutyryl, γ-chlorobutyryl, oxalyl, succinyl, glutamyl, pyroglutamyl, phthalyl or p-toluenesulphonyl, or of the urethane type, such as tert-butyloxycarbonyl, isopropyloxycarbonyl, ethoxycarbonyl, allyloxycarbonyl, cyclohexyloxycarbonyl, benzyloxycarbonyl, p-chlorobenzyloxycarbonyl, p-bromobenzyloxycarbonyl or p-nitrobenzyloxycarbonyl;

R denotes a hydrogen atom or an —SO₃H radical;

A and D are such that:

either (a) one of A and D is a radical of formula:

and the other is a radical of formula:

which m and n each denote an integer from 1 to 5, and A and D form, together with the remainder of the molecule, a ring by amidation of their side chains, or (b) A and D are the same or different and each denotes a radical of formula:

or

which p denotes 1 or 2, and A and D form, together with the remainder of the molecule, a ring by formation of a disulphide bridge between the sulphur atoms of their side chains;

B and E, which may be identical or different, each denote a methionine, norleucine, leucine, serine, threonine or allo-threonine residue, or a cysteine or homocysteine residue, in which the OH or SH groups can be free or protected by
  (i) a straight-or branched-chain alkyl radical containing 1 to 6 carbon atoms or
  (ii) a phenyl radical, which is unsubstituted or substituted with one or more fluorine atoms, or
  (iii) a benzyl radical, which is unsubstituted or substituted with one or more fluorine atoms, or (iv) an alkylcarbonyl radical in which the alkyl portion contains 1 to 5 carbon atoms in a straight or branched chain, or a benzoyl, phenylacetyl or benzhydrylcarbonyl radical in which the phenyl portion is unsubstituted or substituted with one or more fluorine atoms;

F denotes a valency bond or a phenylalanine, O-methyl-tyrosine or cyclohexylalanine residue; and Q denotes a hydrogen atom or an alkyl radical containing 1 to 6 carbon atoms in a straight or branched chain, which is unsubstituted or substituted with one or more fluorine atoms, or a phenyl or phenylalkyl radical in which the alkyl portion contains 1 to 3 carbon atoms in a straight or branched chain and in which the phenyl portion is unsubstituted or substituted with one or more fluorine atoms, each of the aforesaid different amino acid residues being in D, L or DL form; and their pharmaceutically acceptable salts.

According to a feature of the invention, the products of formula (II) are prepared by the action of an acid of formula:

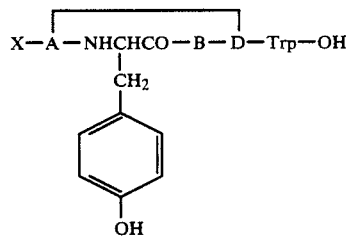

(VII)

in which the symbols are as defined above, on an amine of formula:

H—E—Asp—F—NHQ    (VIII)

in which the symbols are as defined above, followed by a sulphation when it is desired to obtain a product of formula (II) in which R denotes an —SO₃H radical.

The coupling of the products of formula (VII) and (VIII) is accomplished by any method known to those skilled in the art for condensing a peptide with another peptide.

It is especially advantageous to use the compound of formula (VII) in an activated form. Suitable activated forms include the products of reaction of a compound of formula (VII) with hydroxybenzotriazole, N-hydroxysuccinimide, p-nitrophenol or tri- or pentachlorophenyl, in the presence of a condensing agent.

In practice, it is especially advantageous to use, as the activated form, the product of reaction with N-hydroxysuccinimide in an organic solvent, for example an ether such as tetrahydrofuran, a chlorinated solvent such as methylene chloride or chloroform, an amide such as dimethylformamide, or a mixture of these solvents, in the presence of dicyclohexylcarbodiimide at a temperature in the region of 0° C.

The condensation of the compound of formula (VI ) in activated form with the compound of formula (VIII) is generally performed under the same conditions of temperature and reaction medium as those under which the activated form of the compound of formula (VII) has been prepared. It is not, moreover, necessary to isolate this activated form in order to perform the condensation with the compound of formula (VIII).

The subsequent sulphation of the product of condensation of the compounds of formulae (VII) and (VIII) may be accomplished with any known sulphating agent that does not affect the remainder of the molecule. It is especially advantageous to use the SO₃-pyridine complex as sulphating agent, working in an anhydrous organic solvent such as dimethylformamide or pyridine or a mixture of these solvents, at a temperature in the region of 20° C.

The compounds of formula (VII) may be prepared by cyclization of the compounds of formula:

X—A—NHCHCO—B—D—Trp—OH    (IX)
         |
         CH₂
         |
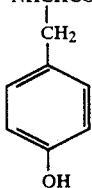
         |
         OH in which the symbols are as defined above, except that A and D are not cyclized together.

When A and D are as defined above in (a), the cyclization is generally accomplished by means of an amidating agent such as diphenylphosphoryl azide, in an organic solvent such as dimethylformamide at a temperature of between −40° C. and 4° C.

When A and D are as defined above in (b), the cyclization is accomplished by oxidation of the side-chain thiols of the groups A and D, either by means of a solution of potassium ferricyanide in water at a pH of 8.0 and at a peptide concentration of 0.3 mM, according to the technique described by SCHILLER et al., Biochem. Biophys. Res. Comm., 101, 337 (1981), or using iodine as oxidizing agent at a peptide concentration of 2 mM in methanol, under the conditions described by SCHLITTER and WEBER, Helv. Chim. Acta., 55, 2061 (1972).

The compounds of formula (IX) may be prepared by the usual methods known in peptide chemistry, for example by the method described above for coupling the compounds of formulae (VII) and (VIII) to one another, or alternatively by the solid-phase sequential method of synthesis known as the Merrifield synthesis.

The compounds of formula (VIII) may also be prepared according to the usual methods of peptide chemistry.

As will be readily noted by those skilled in the art, it is necessary, in order to carry out the process according to the invention, to perform reactions at various stages of the synthesis on products in which the acid, amine, alcohol or thiol groups have had to be protected beforehand. In this case, the protective radical will be removed at the most expedient point of the synthesis, in particular before coupling the amino acids or peptides with one another. Without implied limitation, the groups may be protected, for example, in the following manner:

For the amino groups, the protective radicals listed for the definition of the symbol X above may be used. When blocking is performed on an intermediate product and is hence destined to be removed subsequently, it is advantageous to use a tert-butyloxycarbonyl radical; the latter may then be removed under relatively mild conditions, for example in acid medium by means of trifluoroacetic acid, dilute or otherwise, in methylene chloride, or by means of a solution of gaseous hydrochloric acid in an anhydrous solvent such as dioxane or acetic acid; the peptide or amino acid is then frequently isolated in the form of trifluoroacetate or acetate. The base may be liberated at the desired time using a stronger base such as triethylamine or N,N-diisopropylethylamine.

When, in addition to the N-terminal amine group, there is another amine group carried by the side chain of an amino acid such as lysine, this amine group may be advantageously blocked with another type of radical in order subsequently to unblock the amine groups selectively. In the case of lysine, for example, a benzyloxycarbonyl radical may be employed, which may then be removed by hydrogenolysis in the presence of a catalyst such as palladium on active charcoal.

For the acid groups, the ester radicals usually employed in peptide chemistry, which are readily removable subsequently, may, for example, be used.

It is especially advantageous to block the acid groups in the form of methyl esters, which will then be removed by saponification using an aqueous solution of an alkali metal hydroxide such as sodium hydroxide.

When, in addition to the C-terminal acid group, there is another acid group carried by the side chain of an amino acid such as aspartic acid, this acid group may be advantageously blocked with another type of radical in order subsequently to unblock the acid groups selectively. In the case of aspartic acid, for example, a benzyloxy radical may be employed, which may then be removed by hydrogenolysis in the presence of a catalyst such as palladium on active charcoal.

For the alcohol and thiol groups, the radicals listed at points (i) to (iv) in the definition of the symbols B and E may, for example, be employed. In the case of the thiol groups, it is especially advantageous to use either a 2-nitrophenylsulphenyl radical, which may be removed by reduction using dithiothreitol under the conditions described by SKALA et al., Science, 226, 444 (1984), or an S-acetamidomethyl radical according to the technique of VEBER et coll., J. Am. Chem. Soc., 94, 5456 (1972).

The new products of general formula (II), as well as the synthesis intermediates, may be purified, where appropriate, by the usual methods such as crystallization, chromatography or salt formation.

When the products of general formula (II) possess a free amine group in their molecule, they may be converted to addition salts with acids by the action of an acid, Working in an organic solvent such as an alcohol, a ketone, an ether or a chlorinated solvent. The salt precipitates, where appropriate after concentration of the solution thereof; it is separated by filtration or decantation.

As addition salts with acids, there may be mentioned the salts of inorganic acids, such as hydrochlorides, sulphates or phosphates, and the salts of organic acids, such as acetates, propionates, succinates, benzoates, fumarates, maleates, methanesulphonates, isethionates, theophyllineacetates, salicylates, phenolphthalinates, methylenebis($\beta$-oxynaphthoates) or substitution derivatives of these compounds.

When the products of general formula (II) contain one or more salifiable acid groups in their molecule, it is generally advantageous to isolate them in the form of the sodium or potassium salt. The free acids can then, if so desired, be liberated from their salts according to the usual techniques and, if so desired, be reconverted to another salt with a base.

As salts with bases, there may be mentioned the sodium and potassium salts, or the addition salts with nitrogenous bases, such as the ethanolamine or lysine salts.

The new products of general formula (II) exhibit advantageous pharmacological properties which make them useful in the treatment of nervous diseases of central origin. They have been shown to be active in vitro in tests of affinity for the receptors of the central nervous system, but they are much less active with respect to the receptor sites of the peripheral system (pancreas, intestinal smooth muscles). These properties have been demonstrated, on the one hand, in tests of binding to membranes of mouse brain, and on the other hand in pharmacological tests of release of rat pancreatic amylase and contraction of the guinea-pig ileum.

(1) Binding tests

The products of the invention are tested in competitive experiments with respect to the ligand [$^3$H]BOC-[NLe$^{28,31}$]CCK27-33 on guinea-pig brain cortex and guinea-pig pancreatic acini. The experimental protocols for preparing the tissues and the binding conditions are similar to those described by PELAPRAT et al., tife Sci. 37, 2489 (1985), and DURIEUX et al., Biochem. Biophys. Res. Commun., 137, 1167 (1986). The results are expressed by the inhibition constants $K_I$ in Table I below. The [$^3$H]BOC-[NLe$^{28,31}$]CCK27-33 was used at a concentration of 0.2 nM for the brain and 0.5 nM for the pancreas.

TABLE I

| Products Tested | Binding test guinea-pig cortex $K_I$(in M) | Binding test pancreatic acini $K_I$(in M) | Selectivity factor $S.f. = \dfrac{K_I \text{ pancreas}}{K_I \text{ brain}}$ |
|---|---|---|---|
| Example 5 | 5.10 ± 0.88 × 10$^{-9}$ | 910 ± 140 × 10$^{-9}$ | 179 |
| Example 7 | 6.3 ± 1.23 × 10$^{-9}$ | 1010 ± 110 × 10$^{-9}$ | 160 |
| Example 15 | 4.35 ± 1.10 × 10$^{-9}$ | 860 ± 60 × 10$^{-9}$ | 197 |
| Example 16 | 0.49 ± 0.03 × 10$^{-9}$ | 970 ± 60 × 10$^{-9}$ | 1970 |
| CCK8 (reference) | 0.30 ± 0.07 × 10$^{-9}$ | 0.91 ± 0.26 × 10$^{-9}$ | 3 |

(2) Test of release of pancreatic amylase

The induction of release of amylase by these CCK8 derivatives was tested on guinea-pig pancreatic acini prepared according to the method described by PEIKIN et al., Am. J. Physiol., 235, E 743 (1978). The acini are incubated for 30 minutes at 37° C. in the presence of the test product at different doses, according to the method described by GARDNER and JACKSON, J. Physiol., 270, 439 (1977). The amylase activity is determined using the PHADEBAS reagent (Pharmacia)

according to the method described by CESKA et al., Experientia, 25, 555 (1969).

The results observed are shown in Table II below. The values shown in this table represent the mean of 3 independent experiments, each performed in triplicate.

TABLE II

| Product tested | Secretion of pancreatic amylase by guinea-pig acini | |
|---|---|---|
| | Agonist activity $EC_{50}$ (M) | Antagonist activity $EC_{50}$ (M) |
| Example 5 | $<10^{-5}$ | — |
| Example 7 | $<10^{-5}$ | — |
| Example 16 | $<10^{-5}$ | — |
| CCK8 (reference) | $1.12 + 0.14 \times 10^{-10}$ | — |

(3) Test of contraction-inducing activity on guinea-pig ileum

This test is carried out according to the method described by HUTCHINSON et al., Eur. J. Pharmacol., 69, 87 (1981). Strips of guinea-pig ileum of the terminal portion are rapidly removed and attached in the cell of an isometric gauge containing 25 cm³ of Tyrode's solution. The solution is maintained at 37° C. while a stream of a gas composed of 95% oxygen and 5% $CO_2$ is passed through bubble by bubble. The test compounds are tested under the conditions described by RUIZ-GAYO et al., Peptides, 6, 415 (1985).

The results observed are recorded in Table III. The values shown in this table for the agonist activity represent the mean ($\pm$S.E.M.) of 3 independent experiments. The antagonist activity is measured after inducing contraction by means of $3\times10^{-9}$M CCK8.

TABLE III

| Product tested | Contraction-inducing activity on guinea-pig ileum | |
|---|---|---|
| | Agonist activity $EC_{50}$ (M) | Antagonist activity $EC_{50}$ (M) |
| Example 5 | $>10^{-5}$ | — |
| Example 7 | $>10^{-5}$ | — |
| Example 16 | $>10^{-5}$ | — |
| CCK8 (reference) | $0.68 \pm 0.02 \times 10^{-9}$ | — |

The products of the invention possess rather low toxicity. Their $LD_{50}$ in mice when administered intravenously is generally between 50 and 100 mg/kg.

Of special value are the products of formula (II) in which X denotes hydrogen or tert-butyloxycarbonyl, A and D each denote Asp, Glu, Lys, Orn, Cys or Hcy (in L or D form), R denotes hydrogen or an SO3H radical (the corresponding amino acid being in L or D form), B denotes NLe or Thr (in L form), E denotes NLe or Hcy (S-t-Bu) (in L form), F denotes Phe (in L form), Q denotes hydrogen and Trp and Asp in formula (II) are in L form.

The following products are of very special value:

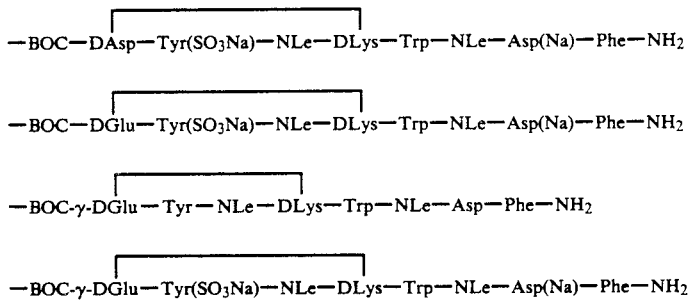

The Examples which follow show how the invention may be put into practice. The reference examples relate to the preparation of the starting materials. In these Examples, the amino acids are represented by the conventional abbreviated form. The peptide chain represented in the text by BOC-γ-DGlu-Tyr- corresponds to amide formation between the γ-carboxyl group of the Glu residue and the α-amino group of the tyrosine (Tyr). The α-carboxyl group of the Glu residue is, in this case, either free, or converted into an amide with the ε-amino group of the lysine side chain according to the formula of the compound. The other abbreviations have the following meanings:

BOC=tert-butyloxycarbonyl
OBZ=benzyloxy
Z=benzyloxycarbonyl
Ac=acetyl
OMe=methoxy
t-Bu=tert-butyl
Suc=succinyl
TFA=trifluoroacetic acid
Nps=2-nitrophenylsulphenyl
Cha=cyclohexylalanine
ONp=4-nitrophenyloxy The mass spectra obtained by FAB ionization were produced on an Ion Tech Ltd magnetic spectrometer at 6 kV with a beam of xenon atoms accelerated to 8 kV.

EXAMPLE 1

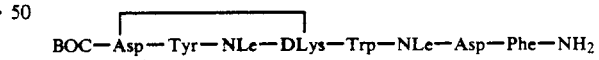

0.136 g of H-NLe-Asp(OBZ)-Phe-NH2, TFA (prepared as described in Reference Example 13) is dissolved in 4 cm³ of dimethylformamide containing 0.035 cm³ of triethylamine. The solution is treated with 0.204 g of

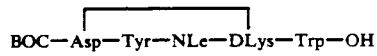

prepared as described in Reference Example (9), 0.029 g of N-hydroxysuccinimide and 0.063 g of dicyclohexylcarbodiimide. The reaction mixture is stirred for one hour at 0° C. and then overnight at a temperature in the region of 20° C. The insoluble material formed is removed by filtration and the filtrate is concentrated to dryness under reduced pressure (1 mm of mercury; 0.13 kPa) at 40° C. The residue obtained is precipitated by a mixture of ethyl acetate and diethyl ether. 0.3 g of

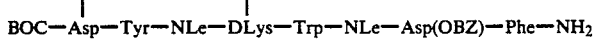

is thereby obtained in the form of a white solid, melting point 130°–133° C.

Rf=0.62 [silica gel; chloroform/methanol (80:20 by volume)].

The unblocking of the acid group of the spartic acid may be performed in the following manner: 11 mg of palladium on active charcoal (content: 10% by weight) are added to a solution of 0.25 g of

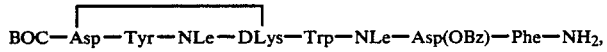

obtained as described above, in 4 cm³ of methanol, and the reaction mixture is hydrogenated at atmospheric pressure at a temperature in the region of 20° C. The catalyst is removed by filtration and the filtrate concentrated to dryness under reduced pressure (20 mm of mercury; 2.7 kPa) at 40° C. 0.216 g of

is thereby obtained.

Rf=0.54 [silica gel : ethylacetate/pyridine/acetic acid/water (80:20:6:11 by volume)].

FAB ionization mass spectrum; m/e=1182 (MH)+
Amino acid analysis:Asp=1.88; NLe=2, Tyr=0.91; Phe=0.98; Lys=0.92.

EXAMPLE 2

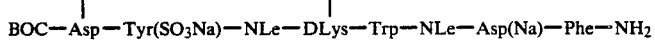

1.1 g of SO₃-pyridine complex is added to a solution of 216 mg of

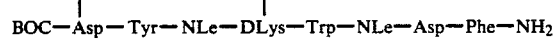

(prepared as described in Example 1) in 2 cm³ of anhydrous dimethylformamide and 6 cm³ of anhydrous pyridine, and the reaction mixture is stirred under a nitrogen atmosphere overnight at a temperature in the region of 20° C. After removal of the solvents under reduced pressure (1 mm of mercury; 0.13 kPa) at 40° C., the residue is taken up with 5 cm³ of aqueous sodium bicarbonate solution and the suspension is stirred for one hour at a temperature in the region of 0° C. while the pH is maintained at a value in the region of 7 by means of saturated aqueous sodium bicarbonate solution. A fraction of product (300 mg) corresponding to the suspended product is collected by centrifugation. A second, less pure fraction (100 mg) is obtained by lyophilization of the aqueous phase and precipitation of the inorganic salts with methanol. These two fractions are combined and purified by chromatography on a column of silica gel (diameter 2 cm), eluting with the mixture of ethyl acetate, pyridine acetic acid and water (60:20:6:11 by volume). 66 mg of

are thereby obtained in the form of a white solid.

Rf=0.23 [silica gel; ethyl acetate/pyridine/acetic acid/water (40:20:6:11 by volume)].

FAB ionization mass spectrum: m/e=1306 (MH)+
Amino acid analysis: Asp=1.91; NLe=2.0; Tyr=0.92; Phe=0.96; Lys=0.93.

By working as described in Examples 1 and 2 above but using the appropriate starting materials, the following were prepared:

EXAMPLE 3

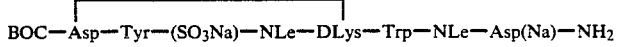

Rf=0.28 silica gel; ethyl acetate/pyridine/acetic acid/water (60:20:6:11 by volume)].

FAB ionization mass spectrum: m/e=1160 (MH)+
Amino acid analysis: Asp=2.02; NLe=2.0; Tyr=0.93; Lys=0.94.

EXAMPLE 4

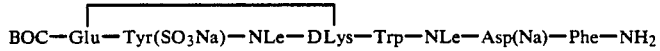

Rf=0.30 [silica gel; ethyl acetate/pyridine/acetic acid/water (60:20:6:11 by volume)].

FAB ionization mass spectrum: m/e=1320 (MH)+
Amino acid analysis: Asp=0.99; Glu=0.95; NLe=2.0; Tyr=0.89; Phe=1.03; Lys=0.96.

EXAMPLE 5

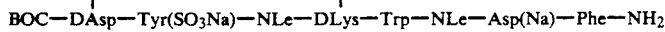

Rf=0.27 [silica gel; ethyl acetate/pyridine/acetic acid/water (60:20:6:11 by volume)].
FAB ionization mass spectrum: m/e=1306 (MH)+
Amino acid analysis: Asp=1.93; NLe=2.0; Tyr=0.93; Phe=0.96; Lys=0.93.

EXAMPLE 6

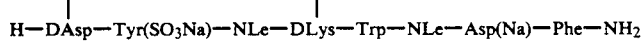

Rf=0.20 [silica gel; ethyl acetate/pyridine/acetic acid/water (40:20:6:11 by volume)].
FAB ionization mass spectrum: m/e=1206 (MH)+
Amino acid analysis: Asp=2.03; NLe=2.0; Tyr=20 0.99; Phe=1.01; Lys=0.96.

EXAMPLE 7

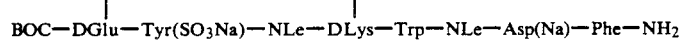

Rf=0.28 [silica gel;ethyl acetate/pyridine/acetic acid/water (60:20:6:11 by volume)].
FAB ionization mass spectrum: m/e=1320 (MH)+
Amino acid analysis: Asp=1.02; Glu=0.97; NLe=2.0; Tyr=0.96; Phe=1.03; Lys=0.99.

EXAMPLE 8

Rf=0.40 [silica gel; ethyl acetate/pyridine/acetic acid/water (40:20:6:11 by volume)].
FAB ionization mass spectrum: m/e=1306 (MH)+
Amino acid analysis: Asp=1.02; Glu=1.00; NLe=2.0; Tyr=0.94; Phe=1.01; Orn=0.96.

EXAMPLE 9

Rf=0.32 [silica gel; ethyl acetate/pyridine/acetic acid/water (60:20:6:11 by volume)].
FAB ionization mass spectrum: m/e=1306 (MH)+
Amino acid analysis: Asp=1.97; NLe=2.0; Tyr=0.95; Phe=1.03; Lys=0.95.

EXAMPLE 10

Rf=0.21 [silica gel; ethyl acetate/pyridine/acetic acid/water) 80:20:6:11 by volume)].
FAB ionization mass spectrum: m/e=1320 (MH)+
Amine acid analysis: Asp=1.02; Glu=1.04;- NLe=2.0; Tyr=0.98; Phe=1.01; Lys=0.98.

EXAMPLE 11

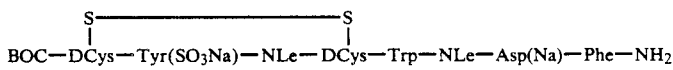

Rf=0.42 [silica gel; ethyl acetate/pyridine/acetic acid/water) 40:20:6:11 by volume)].
FAB ionization mass spectrum: m/e=1284 (MH)+
Amino acid analysis: Asp=1.02; NLe=2.0; Tyr=0.93; Phe=0.99; Cys=1.76.

EXAMPLE 12

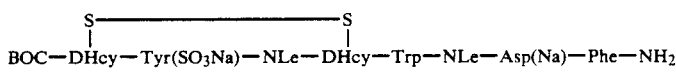

Rf=0.34 [silica gel; ethyl acetate/pyridine/acetic acid/water (60:20:6:11 by volume)].
FAB ionization mass spectrum: m/e=1256 (MH)+
Amino acid analysis: Asp=1.03; NLe=2.0; Hcy=1.81; Tyr=0.96; Phe=1.02.

EXAMPLE 13

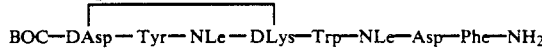

Rf=0.58 [silica gel; ethyl acetate/pyridine/acetic acid/water (80:20:6:11 by volume)].

FAB ionization mass spectrum: m/e=1182 (MH)+
Amino acid analysis: Asp=2.04; NLe=2.0; Tyr=0.94; Phe=1.02; Lys=0.97.

EXAMPLE 14

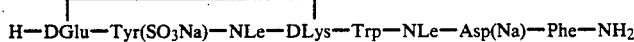

Rf=0.22 [silica gel; ethyl acetate/pyridine/acetic acid/water (60:20:6:11 by volume)].

FAB ionization mass spectrum: m/e=1220 (MH)+
Amino acid analysis: Asp=1.01; Glu=1.03; NLe=2.0; Tyr=0.93; Phe=1.01; Lys=0.98.

EXAMPLE 15

0.235 g of H-NLe-Asp(OBZ)-Phe-NH$_2$.TFA (prepared as described in Reference Example 13) is dissolved in 6 cm$^3$ of dimethylformamide containing 0.054 cm$^3$ of triethylamine. The solution is treated with 0.313 g of

(prepared as described in Reference Example 17), 0.070 g of N-hydroxysuccinimide and 0.095 g of dicyclohexylcarbodiimide. The reaction mixture is stirred for one hour at 0° C. and then overnight at a temperature in the region of 20° C. The insoluble material formed is removed by filtration and the filtrate concentrated to dryness under reduced pressure (1 mm of mercury; 0.13 kPa) at 40° C. The residue obtained is precipitated with a mixture of ethyl acetate and diethylether. 0.48 g of

is thereby obtained in the form of a white solid.

Rf=0.66 [silica gel; ethyl acetate/pyridine/acetic acid water (120:20:6:11 by volume)].

The unblocking of the acid group of the aspartic acid may be performed in the following manner: 40 mg of palladium on active charcoal (content: 10% by weight) is added to a solution of 0.47 g of

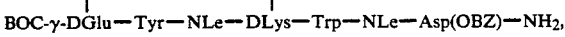

obtained as described above, in 5 cm$^3$ of methanol, and 5 cm$^3$ of dimethylformamide and the reaction mixture is hydrogenated for 2 hours at atmospheric pressure at a temperature in the region of 20° C. The catalyst is removed by filtration and the filtrate concentrated to dryness under reduced pressure (20 mm of mercury; 2.7 kPa) at 40° C. 0.44 g of

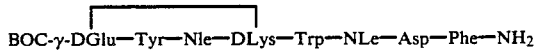

is thereby obtained in the form of a white solid product, melting point 195°–197° C.

Rf=0.30 [silica gel; ethyl acetate/pyridine/acetic acid/water (120:20:6:11 by volume)].

FAB ionization mass spectrum: m/e=1196 (MH)+
Amino acid analysis: Asp=2.03; Glu=1.01; NLe=2.0; Tyr=0.93; Phe=0.99; Lys=0.95.

EXAMPLE 16

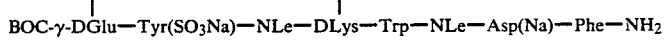

1.3 g of SO$_3$-pyridine complex are added to a solution of 0.23 g of

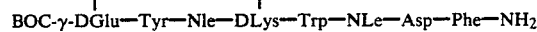

(prepared as described in Example 15) in 2 cm$^3$ of anhydrous dimethylformamide and 6 cm$^3$ of anhydrous pyridine, and the mixture is stirred under a nitrogen atmosphere overnight at a temperature in the region of 20° C. After removal of the solvents under reduced pressure (1 mm of mercury; 0.13 kPa) at 40° C., the residue is taken up with 5 cm$^3$ of saturated aqueous sodium bicarbonate solution and the solution is stirred for one hour at a temperature in the region of 0° C. while the pH is maintained at a value in the region of 7 by means of saturated sodium bicarbonate solution. A fraction of product (250 mg) corresponding to the suspended product is obtained by centrifugation. A second, less pure fraction (120 mg) is obtained by lyophilization of the aqueous phase and precipitation of the inorganic salts with methanol. These two fractions are combined and purified by chromatography on a column of silica gel (diameter: 2 cm), eluting with a mixture of ethyl acetate, pyridine, acetic acid and water (65:20:6:11 by volume). 100 mg of

are thereby obtained in the form of a white solid.

Rf=0.45 [silica gel; butanol/acetic acid/water (4:1:1 by volume)].

FAB ionization mass spectrum: m/e=1320 (MH)+

Amino acid analysis: Asp=0.92; Glu=0.94; NLe=2.0; Tyr=0.94; Phe=1.01; Lys=0.99.

REFERENCE EXAMPLE 1

BOC-DLys(Z)-Trp-OMe 1.69 cm³ of triethylamine is added to a solution, cooled to 0° C., of 2.64 g of methyl tryptophanate hydrochloride in 120 cm³ of a mixture of tetrahydrofuran and chloroform (60:40 by volume), followed by 4.6 g of BOC-DLys(Nε-Z)-OH, 1.8 g of 1-hydroxybenzotriazole and 2.73 g of dicyclohexylcarbodiimide, and the reaction mixture is stirred under a nitrogen atmosphere for one hour at 0° C. and then overnight at a temperature in the region of 20° C. The solid formed is removed by filtration and the filtrate concentrated to dryness under reduced pressure (20 mm of mercury; 2.7 kPa) at a temperature in the region of 40° C. The oil obtained is taken up with ethyl acetate. The solution obtained is washed with 10% strength aqueous citric acid solution, then with saturated aqueous sodium bicarbonate solution and then finally with saturated aqueous sodium chloride solution to neutrality. The organic phase is dried over sodium sulphate, filtered and evaporated to dryness under reduced pressure (20 mm of mercury; 2.7 kPa) at a temperature in the region of 40° C. The residue obtained is recrystallized in a mixture of methyl acetate and hexane. 6.07 g of BOC-DLys(Z)-Trp-OMe, melting point 68°-70° C., are thereby obtained.

Rf=0.53 [silica gel; chloroform/methanol (9:1 by volume)].

REFERENCE EXAMPLE 2

BOC-NLe-DLys(Z)-Trp-OMe 7.5 g of BOC-DLys(Z)-Trp-OMe (prepared as described in Reference Example 1) are dissolved in a mixture, cooled to 0° C., of methylene chloride, trifluoroacetic acid and anisole, 20 cm³, 20 cm³ and 1 cm³, respectively), and the reaction mixture is stirred under nitrogen for 45 minutes at 0° C. and then for 45 minutes at room temperature. The solvents are then evaporated off under reduced pressure (1 mm of mercury; 0.13 kPa) at a temperature in the region of 40° C. The resulting amorphous solid is taken up with 100 cm³ of a mixture, cooled to 0° C., of chloroform and tetrahydrofuran (50:50 by volume), and the mixture is treated successively with 1.81 cm³ of triethylamine, 3 g of N-tert-butyloxycarbonylnorleucine, 1.98 g of 1-hydroxybenzotriazole and 2.67 g of dicyclohexylcarbodiimide. The reaction mixture is stirred under nitrogen for one hour at 0° C. and then overnight at a temperature in the region of 20° C. The solid formed is removed by filtration and the filtrate is concentrated to dryness under reduced pressure (20 mm of mercury; 2.7 kPa) at a temperature in the region of 40° C. The oil obtained is taken up with ethyl acetate. The solution obtained is washed with 10% strength aqueous citric acid solution, then with saturated aqueous sodium bicarbonate solution and then finally with saturated aqueous sodium chloride solution to neutrality. The organic phase is dried over sodium sulphate, filtered and evaporated to dryness under reduced pressure (20 mm of mercury, 2.7 kPa) at a temperature in the region of 40° C. The residue obtained is recrystallized in a mixture of ethyl acetate and diethyl ether. 7.75 g of BOC-NLe-DLys(Z)-Trp-OMe, melting point 80°-82° C., are thereby obtained.

Rf=0.35 [silica gel: chloroform/methanol (95:5 by volume)].

REFERENCE EXAMPLE 3

H-NLe-DLys(Z)-Trp-OMe-TFA 6.2 g of BOC-NLe-DLys(Z)-Trp-OMe (prepared as described in reference Example 2) are dissolved in a mixture, cooled to 0° C., of methylene chloride, trifluoroacetic acid and anisole (15 cm³, 15 cm³ and 0.8 cm³ respectively), and the reaction mixture is stirred under nitrogen for 45 minutes at a temperature in the region of 20° C. The solvents are then evaporated off under reduced pressure (1 mm of mercury; 0.13 kPa) at 40° C., and the residue obtained is purified by flash chromatography of silica gel, eluting with a mixture of chloroform and methanol (95:5 by volume). 5.68 g of H-NLe-DLys(Z)-Trp-OMe-TFA are thereby obtained.

Rf=0.49 [silica gel; chloroform/methanol (80:20 by volume)].

REFERENCE EXAMPLE 4

BOC-Tyr-NLe-DLys(Z)-Trp-OMe 0.68 cm³ of triethylamine, 1.38 g of N-tertbutyloxycarbonyltyrosine, 0.75 g of 1-hydroxybenzotriazole and 1.01 g of dicyclohexylcarbodiimide are added successively to a solution, cooled to 0° C., of 3.46 g of H-NLe-DLys(Z)-Trp-OMe-TFA (prepared as described in Reference Example 3) in 30 cm³ of chloroform. The reaction mixture is stirred under nitrogen for 1 hour at 0° C. and then overnight at a temperature in the region of 20° C. The insoluble material formed is removed by filtration and the filtrate concentrated to dryness under reduced pressure (20 mm of mercury; 2.7 kPa) at 40° C. The oily residue obtained is purified by flash chromatography on silica gel, eluting with a mixture of chloroform and methanol (97:3 by volume). 3.3 g of BOC-Tyr-NLe-DLys(Z)-Trp-OMe, melting point 152°-154° C., are thereby obtained.

Rf=0.46 [silica gel; chloroform/methanol (90:10 by volume)].

REFERENCE EXAMPLE 5

H-Tyr-NLe-DLys(Z)-Trp-OMe-TFA 2.7 g of BOC-Tyr-NLe-DLys(Z)-Trp-OMe (prepared as described in Reference Example 4) are dissolved in a mixture, cooled to 0° C., of methylene chloride, trifluoroacetic acid and anisole (5 cm³, 5 cm³ and 0.2 cm³, respectively), and the reaction mixture is stirred under nitrogen for 45 minutes at a temperature in the region of 0° C. and 45 minutes at a temperature in the region of 20° C. The solvents are then evaporated off under reduced pressure (20 mm of mercury; 2.7 kPa) at 40° C. and the residue obtained is precipitated with diethyl ether. 2.3 g of H-Tyr-NLe-DLys(Z)-Trp-OMe-TFA are thereby obtained.

Rf=0.58 [silica gel; chloroform/methanol (80:20 by volume)].

REFERENCE EXAMPLE 6

BOC-Asp(OBZ)-Tyr-NLe-DLys(Z)-Trp-OMe 0.41 cm³ of N,N-diisopropylamine, 0.64 g of BOC-Asp(OBZ)-ONp and 0.186 g of 1-hydroxybenzotriazole are added successively to a solution, cooled to 0° C., of 1.15 g of H-Tyr-NLe-DLys(Z)-Trp-OMe (prepared as described in Reference Example 5) in 8 cm³ of dimethylformamide, and the reaction mixture is stirred under a nitrogen atmosphere for one hour at 0° C. and then for two hours at a temperature in the region of 20° C. The solvents are then evaporated off under reduced pressure (1 mm of mercury; 0.13 kPa) at 40° C. The oily residue is ground with diethyl ether and the solid obtained recrystallized in a mixture of ethyl acetate and hexane. 1.2 g of BOC-Asp(OBZ)-Tyr-NLe-DLys(Z)-Trp-OMe are thereby obtained in the form of a yellow solid, melting point 182°–184° C.

Rf=0.72 [silica gel; chloroform/methanol (80:20 by volume)].

REFERENCE EXAMPLE 7

BOC-Asp-Tyr-NLe-DLys-Trp-OMe 0.12 g of palladium on active charcoal (10% by weight) is added to a solution of 0.6 g of BOC-Asp(OBZ)-Tyr-NLe-DLys(Z)-Trp-OMe (prepared as described in Reference Example 6) in 20 cm³ of methanol, and the mixture is hydrogenated under atmospheric pressure at a temperature in the region of 20° C. for 2 hours. After removal of the catalyst by filtration, the filtrate is concentrated to dryness under reduced pressure (20 mm of mercury; 2.7 kPa) at 40° C. 4.6 g of BOC-Asp-Tyr-NLe-DLys-Trp-OMe are thereby obtained.

Rf=0.36 silica gel; ethyl acetate/pyridine/acetic acid/water (40:20:6:11 by volume)].

REFERENCE EXAMPLE 8

```
┌─────────────────────────────┐
BOC—Asp—Tyr—NLe—DLys—Trp—OMe
```

A solution of 0.248 cm³ of diphenylphosphoryl azide in 5 cm³ of dimethylformamide is added dropwise and with stirring in the space of one hour to a solution, cooled to −40° C. and stored under a nitrogen atmosphere, of 0.74 g of BOC-Asp-Tyr-NLe-DLys-Trp-OMe (prepared as described in Reference Example 7) in 145 cm³ of dimethylformamide containing 0.246 cm³ of triethylamine, and stirring is continued for 48 hours at a temperature in the region of −25° C. and then for 48 hours at 0° C. Throughout the reaction, the apparent pH of the reaction medium is maintained at between 7 and 7.5 by adding triethylamine. The reaction mixture is then concentrated to dryness under reduced pressure (1 mm of mercury; 0.13 kPa) at 40° C. The oil obtained is purified by flash chromatography on silica gel, eluting with a mixture of chloroform and methanol (95:5 by volume). 0.37 g of white solid, melting point 172°–174° C., is thereby obtained.

Rf=0.31 [silica gel; chloroform/methanol (90:10 by volume)].

FAB ionization mass spectrum: m/e=806 (MH)+

REFERENCE EXAMPLE 9

```
┌─────────────────────────────┐
BOC—Asp—Tyr—NLe—DLys—Trp—OH
```

0.8 cm³ of 1N aqueous sodium hydroxide solution is added to a solution, cooled to approximately 0° C., of 0.33 g of

```
┌─────────────────────────────┐
BOC—Asp—Tyr—NLe—DLys—Trp—OMe
```

(prepared as described in Reference Example 8) in 4.5 cm³ of methanol, and the reaction mixture is stirred under nitrogen for 2 hours at 0° C. and then overnight at a temperature in the region of 20° C. The reaction mixture is concentrated to dryness under reduced pressure (20 mm of mercury; 2.7 kPa) at 40° C. and the residue is dissolved in 5 cm³ of distilled water. The solution obtained is extracted with diethyl ether and the organic phase removed; the aqueous phase is acidified to 0° C. with 1N aqueous hydrochloric acid solution and then extracted with ethyl acetate. The organic solution is washed with saturated aqueous sodium chloride solution, then dried over sodium sulphate and filtered. The filtrate is concentrated to dryness under reduced pressure (20 mm of mercury; 2.7 kPa) at 40° C. 0.24 g of

```
┌─────────────────────────────┐
BOC—Asp—Tyr—NLe—DLys—Trp—OH,
``` melting point 205°–207° C., is thereby obtained.

Rf=0.37 [silica gel; ethyl acetate[pyridine/acetic acid/water (80:20:6:11 by volume).

REFERENCE EXAMPLE 10

BOC-Asp(OBZ)-Phe-NH₂

1.86 g of BOC-Asp(OBZ)-ONp are added to a solution, cooled to 0° C., of 1.07 g of phenylalanine trifluoroacetate in 10 cm³ of dimethylformamide containing 0.6 cm³ of triethylamine, and the reaction mixture is stirred at a temperature in the region of 20° C. for 24 hours. The reaction mixture is concentrated to dryness under reduced pressure (1 mm of mercury; 0.13 kPa) at 40° C. The residue obtained is taken up with ethyl acetate. The solution obtained is washed with 10% strength aqueous citric acid solution, then with saturated aqueous sodium bicarbonate solution and then finally with saturated aqueous sodium chloride solution to neutrality. The organic phase is dried over sodium sulphate, filtered and evaporated to dryness under reduced pressure (20 mm of mercury; 2.7 kPa) at a temperature in the region of 40° C. The residue obtained is recrystallized in a mixture of ethyl acetate and hexane. 1.47 g of BOC-Asp(OBZ)-Phe-NH2 are thereby obtained in the form of a white solid, melting point 137°–138° C.

Rf=0.38 [silica gel; chloroform/methanol (95:5 by volume)].

REFERENCE EXAMPLE 11

H-Asp-(OBZ)-Phe-NH₂.TFA 1 g of BOC-Asp(OBZ)-Phe-NH2 (prepared as described in Reference Example 10) is dissolved in a mixture, cooled to 0° C., of methylene chloride and trifluoroacetic acid (2.5 cm³, 2.5 cm³), and the reaction mixture is stirred for 45 minutes at 0° C. and for 45 minutes at a temperature in the region of 20° C. The solvents are then evaporated off under reduced pressure (20 mm of mercury; 2.7 kPa) at 40° C. The residue obtained is rendered solid with diethyl ether. 1.85 g of H-Asp(OBZ)-Phe-NH₂. TFA are thereby obtained.

Rf=0.23 [silica gel; chloroform/methanol (90:10 by volume)].

REFERENCE EXAMPLE 12

BOC-NLe-Asp(OBZ)-Phe-NH$_2$ 1.48 g of BOC-NLe-ONp and 0.578 g of 2-hydroxybenzotriazole are added to a solution, cooled to 0° C., 1.83 g of H-Asp(OBZ)-Phe-NH$_2$. TFA (prepared as described in Reference Example 11) in 20 cm$^3$ of dimethylformamide containing 1.3 cm$^3$ of N,N-diisopropylethylamine, and the reaction mixture is stirred for 30 minutes at 0° C. and then overnight at a temperature in the region of 20° C. After evaporation of the solvent under reduced pressure (1 mm of mercury; 0.13 kPa) at 40° C., the oily residue obtained is precipitated with a mixture of ethyl acetate and hexane. 1.98 g of BOC-NLe-Asp(OBZ)-Phe-NH$_2$ are thereby obtained in the form of a white solid, melting point 134°-136° C.

Rf=0.61 [silica gel; chloroform/methanol (90:10 by volume)].

REFERENCE EXAMPLE 13

H-NLe-Asp(OBZ)-Phe-NH$_2$. TFA 0.151 g of BOC-NLe-Asp(OBZ)-Phe-NH$_2$ (prepared as described in Reference Example 12) is dissolved in a mixture, cooled to 0° C., of methylene chloride and trifluoroacetic acid (1 cm$^3$ and 1 cm$^3$ respectively), and the reaction mixture is stirred for 45 minutes at 0° C. and 45 minutes at a temperature in the region of 20° C. The mixture is concentrated to dryness under reduced pressure (20 mm of mercury; 2.7 kPa) at 40° C. 0.136 g of H-NLe-Asp(OBZ)-Phe-NH$_2$. TFA is thereby obtained.

Rf=0.30 [silica gel; chloroform/ethanol (80:20 by volume)].

REFERENCE EXAMPLE 14

BOC-γ-DGlu(βOBZ)-Tyr-NLe-DLys(Z)-Trp-OCH$_3$ 0.204 cm$^3$ of triethylamine, 0.49 g of BOC-DGlu-(αOBZ)-OH, 0.17 g of hydroxysuccinimide and 0.30 9 of dicyclohexylcarbodiimide are added successively to a solution, cooled to 0° C., of 1.29 g of H-Tyr-NLe-DLys-(Z)-Trp-OCH$_3$ (prepared as described in Reference Example 5) in 10 cm$^3$ of dimethylformamide. The reaction mixture is stirred under nitrogen for one hour at 0° C. and then overnight at a temperature in the region of 20° C. The insoluble material formed is removed by filtration and the filtrate concentrated to dryness under reduced pressure (20 mm of mercury; 2.7 kPa) at 40° C. The oily residue is purified by precipitation with ethyl acetate, to yield 1.3 g of BOC-γ-DGlu(α-OBZ)-Tyr-NLe-DLys(Z)-Trp-OCH$_3$, melting point 110°-113° C.

Rf=0.48 [silica gel; chloroform/methanol (90:10 by volume)].

REFERENCE EXAMPLE 15

BOC-γ-DGlu-Tyr-NLe-DLys-Trp-OCH$_3$ 0.16 g of palladium on active charcoal (10% by weight) is added to a solution of 1.27 g of BOC-γ-DGlu-(α-OBZ)-Tyr-NLe-Dlys(Z)-Trp-OMe (prepared as described in Reference Example 14) in 30 cm$^3$ of methanol, and the mixture is hydrogenated at atmospheric pressure at a temperature in the region of 20° C. for 3 hours. After removal of the catalyst by filtration, the filtrate is concentrated to dryness under reduced pressure (20 mm of mercury; 2.7 kPa) at 40° C. 0.99 g of BOC-γ-DGlu-Tyr-NLe-DLys-Trp-OCH$_3$, melting point 155°-157° C., is thereby obtained.

Rf=0.37 [silica gel; chloroform/methanol (70:30 by volume)].

REFERENCE EXAMPLE 16

BOC-γ-DGlu—Tyr—NLe—DLys—Trp—OCH$_3$
⌐⎯⎯⎯⎯⎯⎯⎯⎯⎯⎯⎯⎯⎯⎯⎯⎯⎯⎯⎯¬

A solution of 0.258 cm$^3$ of diphenylphosphoryl azide in 5 cm$^3$ of dimethylformamide is added dropwise and with stirring in the space of one hour to a solution, cooled to −40° C. and stored under a nitrogen atmosphere, of 0.86 g of BOC-γ-DGlu-Tyr-NLe-DLys-Trp-OCH$_3$ (prepared as described in Reference Example 15) in 175 cm$^3$ of dimethylformamide containing 0.282 cm$^3$ of triethylamine, and stirring is continued for 48 hours at a temperature in the region of −25° C. and then for 48 hours at 0° C. Throughout the reaction, the apparent pH of the reaction medium is maintained at between 7 and 7.5 by adding triethylamine. The reaction mixture is then concentrated to dryness under reduced pressure (1 mm of mercury; 0.13 kPa) at 40° C. The oil obtained is purified by flash chromatography on silica gel, eluting with a mixture of chloroform and methanol (95:5 by volume). 0.59 g of white solid, melting point 170°-172° C., is thereby obtained.

Rf=0.65 [silica gel; chloroform/methanol (9:1 by volume)].

FAB ionization mass spectrum: m/e=820 (MH)$^+$

REFERENCE EXAMPLE 17

BOC-γ-DGlu—Tyr—NLe—DLys—Trp—OH
⌐⎯⎯⎯⎯⎯⎯⎯⎯⎯⎯⎯⎯⎯⎯⎯⎯⎯¬

1.1 cm$^3$ of 1N aqueous sodium hydroxide solution is added to a solution, cooled to approximately 0° C., of 0.45 g of BOC-γ-DGlu—Tyr—NLe—DLys—Trp—OCH$_3$
⌐⎯⎯⎯⎯⎯⎯⎯⎯⎯⎯⎯⎯⎯⎯⎯⎯⎯⎯¬

(prepared as described in Reference Example 16) in 6 cm$^3$ of methanol, and the reaction mixture is stirred under nitrogen for 2 hours at 0° C. and overnight at a temperature in the region of 20° C. The reaction mixture is concentrated to dryness under reduced pressure (20 mm of mercury; 2.7 kPa) at 40° C. and the residue is dissolved in 5 cm$^3$ of distilled water. The solution obtained is extracted with diethyl ether and the organic phase removed; the aqueous phase is acidified at 0° C. with 1N aqueous hydrochloric acid solution and then extracted with ethyl acetate. The organic solution is washed with saturated aqueous sodium chloride solution, then dried over sodium sulphate and filtered. The filtrate is concentrated to dryness under reduced pressure (20 mm of mercury; 2.7 kPa) at 40° C. 0.31 g of BOC-γ-DGlu—Tyr—NLe—DLys—Trp—OH,
⌐⎯⎯⎯⎯⎯⎯⎯⎯⎯⎯⎯⎯⎯⎯⎯⎯⎯¬ a white solid, melting point 181°-182° C., is thereby obtained.

Rf=0.30 [silica gel; ethyl acetate/pyridine/acetic acid/water (120:20:6:11 by volume)].

The present invention also provides pharmaceutical compositions comprising at least one compound of formula (II), in free form or in the form of an addition salt with a pharmaceutically acceptable acid or base, in combination with one or more compatible and pharmaceutically acceptable products, which may be inert or physiologically active, and in particular one or more diluents or adjuvants. The compositions according to the invention can be used orally, parenterally, rectally or in the form of patches.

As solid compositions for oral administration, tablets, pills, powders (in particular, in gelatin capsules or wafer capsules) or granules may be used. In these compositions, the active product according to the invention is mixed with one or more inert diluents such as starch, cellulose, sucrose, lactose or silica. These compositions can also contain substances other than diluents, for example one or more lubricants such as magnesium stearate or talc, a colouring, a coating (dragées) or a lacquer.

As liquid compositions for oral administration, it is possible to use solutions, suspensions, emulsions, syrups and elixirs that are pharmaceutically acceptable, containing inert diluents such as water, ethanol, glycerol, vegetable oils or liquid paraffin. These compositions can also contain substances other than diluents, for example wetting, sweetening, thickening, flavouring or stabilizing products.

The sterile compositions for parenteral administration can preferably be solutions, aqueous or otherwise, suspensions or emulsions. As solvent or vehicle, water, propylene glycol, a polyethylene glycol, vegetable oils, especially olive oil, injectable organic esters, for example ethyl oleate or other suitable organic solvents may be employed. These compositions can also contain adjuvants, especially wetting, tonicity-regulating, emulsifying, dispersing and stabilizing agents. The sterilization can be carried out in several ways, for example by aseptic filtration, by incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules which contain, apart from the active product, excipients such as cocoa butter, semi-synthetic glycerides or polyethylene glycols.

In human therapy, the products according to the invention are especially useful in the treatment of conditions of the central nervous system in which a dysfunction of the dopaminergic pathways occurs, for example in Parkinson's disease, choreas, schizophrenia, tardive dyskinesias or manic-depressive episodes.

The dosages depend on the desired effect and the treatment period; they are generally between 2 and 10 mg per day parenterally for an adult, in one or more doses.

Generally speaking, the doctor will determine the dosage which he judges to be most suitable in accordance with the age, the weight and all other factors specific to the subject to be treated.

The Example which follows illustrates compositions according to the invention.

EXAMPLE

An injectable solution is prepared containing 1 mg of active product and having the following composition:

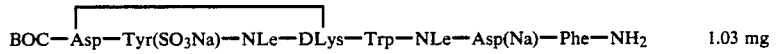  1.03 mg or

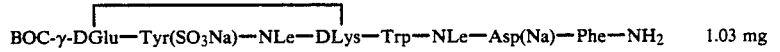  1.03 mg distilled water   q.s. 2 cm³

We claim:

1. The peptide which is

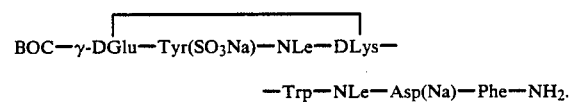

2. A pharmaceutical composition useful in the treatment of conditions of the central nervous system in which a disfunction of the dopaminergic pathways occurs comprising:
a pharmaceutically effective amount of a compound as defined in claim 1, in free form or in the form of an addition salt with a pharmaceutically acceptable acid or base, in combination with one or more diluents or adjuvants that are compatible and pharmaceutically acceptable.

* * * * *